United States Patent [19]

Pitchai et al.

[11] Patent Number: 5,233,093

[45] Date of Patent: Aug. 3, 1993

[54] HYDROFORMYLATION PROCESS AND BIMETALLIC CATALYST THEREFOR

[75] Inventors: Rangasamy Pitchai; Anne M. Gaffney, both of West Chester; Manish K. Nandi, Wayne; Yuan-Zhang Han, West Chester, all of Pa.

[73] Assignee: ARCO Chemical Technology, L.P., Wilmington, Del.

[21] Appl. No.: 916,575

[22] Filed: Jul. 20, 1992

[51] Int. Cl.$^5$ .............................................. C07C 45/50
[52] U.S. Cl. .................................... 568/454; 568/452; 568/451
[58] Field of Search ............................... 568/451, 454

[56] References Cited

U.S. PATENT DOCUMENTS

| | | | |
|---|---|---|---|
| 3,239,566 | 3/1966 | Slaugh et al. | 260/604 |
| 3,631,111 | 12/1971 | Tucci | 260/604 |
| 4,143,075 | 3/1979 | Bryant | 260/604 |
| 4,200,591 | 4/1980 | Hignett et al. | 260/604 |
| 4,200,592 | 4/1980 | Hignett | 260/604 |
| 4,215,077 | 7/1980 | Matsumoto et al. | 568/454 |
| 4,226,845 | 10/1980 | Laine | 423/655 |
| 4,262,141 | 4/1981 | Richter et al. | 568/454 |
| 4,306,084 | 12/1981 | Pettit | 568/451 |
| 4,388,477 | 6/1983 | Cooper | 568/451 |
| 4,453,019 | 6/1984 | Chang | 568/454 |
| 4,506,101 | 3/1985 | Chang | 568/454 |
| 4,599,323 | 7/1986 | Demay et al. | 502/161 |
| 4,996,366 | 2/1991 | Tinucci et al. | 568/454 |
| 5,012,008 | 4/1991 | Drago et al. | 568/454 |

FOREIGN PATENT DOCUMENTS 2840168  3/1980  Fed. Rep. of Germany ...... 568/454

*Primary Examiner*—Werren B. Lone
*Attorney, Agent, or Firm*—Jonathan L. Schuchardt

[57] ABSTRACT

An improved allyl alcohol hydroformylation process and catalyst are disclosed. The process uses a catalyst system comprising a Group VIII metal carbonyl complex catalyst, a trisubstituted phosphine, a neutral Group VIII(a) metal complex cocatalyst, and optionally, a diphosphinoalkane. The process uniquely gives an enhanced linear:branched aldehyde product ratio.

13 Claims, No Drawings

HYDROFORMYLATION PROCESS AND BIMETALLIC CATALYST THEREFOR

FIELD OF THE INVENTION

The invention relates to hydroformylation of allyl alcohol, and more particularly, to a process for hydroformylating allyl alcohol using a homogeneous, bimetallic catalyst.

BACKGROUND OF THE INVENTION

Hydroformylation of olefins in the presence of Group VIII transition metal carbonyl complex catalysts to produce aldehydes is well known. Rhodium complexes such as $HRh(CO)(PPh_3)_3$ are favored because they are active under mild conditions and are highly selective toward linear aldehyde products. Since rhodium is expensive, catalyst lifetime is important for commercial hydroformylation processes that use such rhodium catalysts. Matsumoto et al. (U.S. Pat. No. 4,215,077) teach to prolong the lifetime of rhodium catalysts by including a diphosphinoalkane in the process. Catalyst lifetime improves; however, the ratio of linear to branched aldehyde products is limited when a diphosphinoalkane is used. For example, the linear/branched ratio of aldehydes is typically about 7:1 at best when the catalysts of U.S. Pat. No. 4,215,077 are used to hydroformylate allyl alcohol. Higher selectivity to the linear aldehydes is desirable because the linear end-products are often more valuable than those derived from branched aldehydes.

Hydroformylation catalysts containing more than one Group VIII metal compound are known. Chang (U.S. Pat. No. 4,453,019) teaches the use of mixed metal catalysts in the hydroformylation of olefins to produce linear aldehydes and alcohols. The catalyst system includes a first transition metal compound, which may be a neutral Group VIII metal complex such as $HRh(CO)(PPh_3)_3$, and an anionic transition metal compound of the formula $M^{+n}[H_yA_xL_x]^{-n}$ wherein A can be a Group VIII(a) metal (iron, ruthenium, osmium). The latter anionic complexes are prepared by deprotonation of metal hydride compounds or reduction of neutral metal carbonyls. The preferred olefins are unfunctionalized olefins, since hydroxyl groups and halogens are known to deactivate the catalysts (column 3, lines 30-35).

Cooper (U.S. Pat. No. 4,388,477) teaches a hydroformylation process that employs an unmodified rhodium-cobalt catalyst. This bimetallic catalyst gives a relatively high proportion of branched aldehydes with unfunctionalized olefins such as propylene.

Pettit (U.S. Pat. No. 4,306,084) teaches to use a ruthenium carbonyl catalyst under basic conditions (pH 8-11) in aqueous media to selectively give linear aldehyde and alcohol products from the hydroformylation of unfunctionalized olefins such as propylene and 1-butene. Similarly, Laine (U.S. Pat. No. 4,226,845) teaches to use two or more Group VIII metal carbonyl compounds, one of which is ruthenium, in the presence of a base to hydroformylate unfunctionalized olefins.

Hignett et al. (U.S. Pat. No. 4,200,592) teach a homogeneous catalyst system for isomerization and hydroformylation of internal olefins to give linear aldehydes. The catalyst system includes a Rh(I) complex and a complex of a transition metal other than rhodium from Group VI or Group VIII. Only unfunctionalized olefins are used, and the linear/branched aldehyde product ratios reported are typically less than 2:1.

Slaugh (U.S. Pat. No. 3,239,566) teaches to hydroformylate olefins with rhodium or ruthenium-containing catalysts. Bimetallic catalyst systems are not taught, and the examples are specific to unfunctionalized olefins.

Still lacking in the art is a hydroformylation process that gives high selectivity to linear aldehydes, particularly when allyl alcohol is used. Catalysts that have a reduced tendency to deactivate during hydroformylation—yet still give good selectivity to linear aldehydes—are needed.

SUMMARY OF THE INVENTION

An object of the invention is to provide an improved hydroformylation process for allyl alcohol. Another object is to identify bimetallic catalyst systems that have good activity, long lifetimes, and give high selectivity to 4-hydroxybutanal in allyl alcohol hydroformylations.

The invention is an improved hydroformylation process. The process comprises reacting allyl alcohol with hydrogen and carbon monoxide in the presence of a homogeneous catalyst system. The catalyst system includes a Group VIII metal carbonyl complex catalyst, a trisubstituted phosphine, a neutral Group VIII(a) metal complex cocatalyst, and optionally, a diphosphinoalkane. The reaction product is an aldehyde mixture that has a linear to branched mole ratio greater than about 10:1.

The catalyst system of the invention includes a Group VIII metal carbonyl complex, preferably a rhodium hydridocarbonyl complex such as $HRh(CO)(PPh_3)_3$, a trisubstituted phosphine, and a neutral Group VIII(a) metal complex cocatalyst, i.e., a neutral complex that contains iron, ruthenium, or osmium.

DETAILED DESCRIPTION OF THE INVENTION

In the process of the invention, allyl alcohol reacts with hydrogen and carbon monoxide in the presence of a Group VIII metal carbonyl complex catalyst, a trisubstituted phosphine, and a neutral Group VIII(a) metal complex cocatalyst to produce a mixture of 4-hydroxybutanal and 3-hydroxy-2-methylpropanal.

The homogeneous catalyst system of the invention includes a Group VIII metal carbonyl complex catalyst. The catalyst either contains a carbonyl moiety or can be converted to a carbonyl complex in the presence of carbon monoxide. Group VIII metal halides, sulfates, nitrates, and carboxylates are examples of compounds that can be converted to carbonyl complexes in situ by reaction with hydrogen and carbon monoxide.

Examples of suitable Group VIII metal carbonyl complexes or compounds convertable to carbonyl complexes include, but are not limited to, $RhCl_3$, $RuCl_3$, $Rh(CO)_2Cl_2$, $Co_2(CO)_8$, $Rh_6(CO)_{16}$, $Ru_3(CO)_{12}$, $Fe_3(CO)_{12}$, $HRh(CO)(PPh_3)_3$, $H_2Ru_4(CO)_{13}$, $H_2Ru_6(CO)_{18}$, $H_2PtCl_6$, $Rh_4(CO)_{12}$, and the like, and mixtures thereof. Rhodium (I) complexes are preferred. Rhodium complexes of the general formula $HRh(CO)(PR_3)_3$ wherein R is alkyl or aryl are particularly preferred.

The Group VIII metal carbonyl complex catalyst is used in the organic reaction mixture at a metal concentration within the range of about 1 ppm to about 500 ppm; a more preferred range is from about 60 to about 200 ppm.

An excess amount of a trisubstituted phosphine is used in combination with the catalyst to improve its lifetime and selectivity to 4-hydroxybutanal. The proportion of the trisubstituted phosphine used is within the range of about 10 to about 500 equivalents per Group VIII metal atom; a more preferred range is from about 50 to about 250 equivalents. Suitable trisubstituted phosphines for use in the invention include triaryl phosphines, triaryl phosphites, alkyldiarylphosphines, and the like, and mixtures thereof. Particular examples are triphenylphosphine, tritolylphosphine, triphenylphosphite, and n-butyldiphenylphosphine.

A diphosphinoalkane, such as those described in detail in U.S. Pat. No. 4,215,077 (Matsumoto et al.) is optionally used in combination with the catalyst system. The use of a diphosphinoalkane often prolongs the lifetime of the Group VIII metal carbonyl complex catalyst. Examples of suitable diphosphinoalkanes for use in the present invention are those described in U.S. Pat. No. 4,215,077, the teachings of which are incorporated herein by reference in their entirety.

Any desired amount of diphosphinoalkane can be used. Preferably, an amount within the range of about 0.2 to 2.5 equivalents per Group VIII metal atom in the Group VIII metal carbonyl complex catalyst is used. A more preferred range is from about 0.25 to about 1.25 equivalents.

The catalyst system also includes a neutral Group VIII(a) metal complex cocatalyst. Group VIII(a) metals are iron, ruthenium, and osmium. Neutral metal complexes are coordination complexes in which the central metal and its surrounding ligands form a neutral species. Examples of such compounds are $RuCl_3$, $Ru_3(CO)_{12}$, $H_2Ru_4(CO)_{13}$, $Fe_2(CO)_9$, and the like. These neutral complexes should be distinguished from anionic transition metal complexes of the type described in U.S. Pat. No. 4,453,019 beginning at column 4, line 31 of the reference. In an anionic transition metal complex, the central metal and surrounding ligands carry a negative charge that is balanced by the presence of a Group IA metal, Group IIA metal, or an organic cation.

Preferably, the neutral Group VIII(a) metal complex is a carbonyl complex or is readily converted to a neutral carbonyl complex in the presence of carbon monoxide/hydrogen mixtures.

The neutral Group VIII(a) metal complex cocatalysts of the invention are preferably water-stable; i.e., the preferred cocatalyst will not precipitate from the organic reaction mixture when the mixture is exposed to aqueous extraction.

The neutral Group VIII(a) metal complex cocatalyst is preferably used in excess compared with the amount of Group VIII metal carbonyl catalyst. The relative weight ratio of cocatalyst metal:catalyst metal used is preferably within the range of about 1:1 to about 10:1. A more preferred range is from about 3:1 to about 6:1; most preferred is the range from about 4:1 to about 5:1. The cocatalyst metal is typically present in the reaction mixture at a concentration within the range of about 1 ppm to about 5000 ppm; a more preferred range is from about 50 ppm to about 1000 ppm.

The process of the invention is typically performed by feeding a gaseous mixture of carbon monoxide and hydrogen into an organic solution that contains allyl alcohol and the homogeneous catalyst system. The process is preferably performed at a temperature within the range of about 25° C. to about 150° C. A more preferred range is from about 40° C. to about 80° C.; most preferred is the range from about 60° C. to about 70° C.

The total pressure of the system is preferably less than about 30 atmospheres; particularly preferred is the range from about 1 to about 3 atmospheres. The partial pressure ratio of hydrogen to carbon monoxide is preferably within the range of about 1:15 to about 5:1; a more preferred range is from about 1:1 to about 4:1. Inert gases such as nitrogen, helium, argon, methane, and the like can be used in the process as gaseous diluents.

The process of the invention is preferably performed in the presence of an inert organic solvent. Allyl alcohol, the trisubstituted phosphine, the Group VIII metal carbonyl complex catalyst, and the neutral Group VIII(a) metal complex cocatalyst should be at least partially soluble in the organic solvent. Suitable solvents include aromatic and aliphatic hydrocarbons, halogenated hydrocarbons, ethers, ketones, esters, and the like, and mixtures thereof. Specific examples of suitable solvents include benzene, toluene, xylenes, cyclohexane, heptane, methyl ethyl ketone, acetone, ethyl acetate, tetrahydrofuran, dichloromethane, chlorobenzene, and the like. Aromatic hydrocarbons such as toluene and xylenes are preferred.

The process of the invention can be performed batch-wise, semi-continuously, or continuously as desired. A continuous process is preferred.

The aldehyde products can be recovered from the reaction mixture by any convenient means, including distillation, extraction, and the like. Preferably, the aldehydes are isolated by extraction of the organic reaction mixture with water. Aromatic hydrocarbons are preferably used as organic solvents when aqueous extraction is used.

Important advantages of the invention:

(1) The product mixture contains an unusually high proportion of linear aldehyde. Conventional processes for hydroformylating allyl alcohol to 4-hydroxybutanal typically give linear:branched (L/B) aldehyde ratios of about 7:1 or less; the process of the present invention uniquely gives L/B ratios greater than about 10:1, and even greater than 20:1. This is an important advantage because 4-hydroxybutanal is generally regarded as the more valuable of the two aldehyde products.

(2) The rate of reaction is often enhanced by the presence of the neutral Group VIII(a) metal complex cocatalyst. Hydroformylation of allyl alcohol is normally complete in a batch process at 60° C. with 120 ppm rhodium after about 4 hours; with the cocatalyst present, the reaction is essentially complete after 2 hours.

(3) Catalyst activity remains high even when the catalyst is recovered from the reaction mixture and recycled. Selectivity to 4-hydroxybutanal remains high through numerous catalyst recycles.

The following examples merely illustrate the invention. Those skilled in the art will recognize numerous variations that are within the spirit of the invention and scope of the claims.

HYDROFORMYLATION OF ALLYL ALCOHOL

General Procedure

Batch hydroformylations are performed in dry glassware. The apparatus consists of a 500-mL, 5-neck round-bottom flask equipped with mechanical stirrer, condenser, thermocouple, sample port, and gas inlet. The gaseous $H_2/CO$ mixture is sparged into the reaction solvent through a glass tube with a fritted end. Exit gases pass through a toluene trap (dry ice/isopropanol) and a carbon trap before venting to the fume hood.

The reactor is charged with $HRh(CO)(PPh_3)_3$, cocatalyst ($Fe_2(CO)_9$ or $Ru_3(CO)_{12}$), triphenylphosphine, and 1,4-bis(diphenylphosphino)butane (DPB), and is flushed with nitrogen for 15 min. A second jacketed round-bottom flask is charged with toluene (100 mL) and is also flushed with nitrogen for 15 min. The toluene is transferred to the reaction vessel by canula. A flow of $H_2/CO$ gas mixture is started in the reaction vessel. The second round-bottom flask is recharged with toluene (100 mL) and allyl alcohol (24 mL) and is purged with nitrogen. The contents of both flasks are heated to 60° C. Once the reaction temperature is reached, the allyl alcohol solution is rapidly transferred by canula to the reaction vessel. The finish of the transfer is noted as the starting time for the reaction. Samples are periodically withdrawn and analyzed by gas chromatography to determine product composition. Reactions are terminated after 4 hours.

EXAMPLES 1-10

Allyl alcohol is hydroformylated using the general procedure outlined above. Results for Examples 1-10 appear in Table 1. In the examples of the invention (Examples 2-8 and 10), iron nonacarbonyl is used as a cocatalyst either with or without 1,4-bis(diphenylphosphino)butane (DPB) present. The presence of the iron cocatalyst has favorable effects: the rate of reaction increases, and most important, the selectivity to the linear aldehyde improves. The improvement in selectivity occurs with or without DPB being present (compare Examples C1 and 3 with C9 and 10). Selectivity to the linear product also remains high when the rhodium concentration is decreased by 33% (compare Examples 4 and 8). The high selectivity to the linear aldehyde is remarkable and valuable because linear:branched (L/B) ratios greater than about 7:1 have not been previously demonstrated with the commercially important $HRh(CO)(PPh_3)_3$/triphenylphosphine/DPB catalyst system.

EXAMPLES 11-11F

Allyl alcohol is hydroformylated using the general procedure outlined above. After 4 h of reaction time, the catalyst mixture is recovered and reused to hydroformylate a fresh batch of allyl alcohol. Results from 6 consecutive recycle runs with the same catalyst (conventional rhodium catalyst modified by addition of $Fe_2(CO)_9$) appear in Table 2. Catalyst activity remains good; selectivity to the linear aldehyde stays high (L/B=10-20), and even improves somewhat with recycling. Thus, the catalyst life-prolonging effect of DPB is maintained, but selectivity to the linear aldehyde is higher than possible in the absence of the iron cocatalyst.

EXAMPLES 12-12F

Allyl alcohol is hydroformylated using the general procedure outlined above. The rhodium catalyst is modified by the addition of $Ru_3(CO)_{12}$. After 4 h of reaction time, the catalyst is recovered and reused to hydroformylate a fresh batch of allyl alcohol. Results from 6 consecutive recycle runs using the same catalyst system appear in Table 3. Catalyst activity remains good, and selectivity to the linear aldehyde remains high (L/B=10-13). The results parallel those from Examples 11-11F, which use $Fe_2(CO)_9$ as a cocatalyst.

EXAMPLES 13-13B

The procedure of Examples 12-12F is followed, except that DPB is omitted. Good catalyst activity and high selectivity to the linear aldehyde (L/B=15-17) are observed through two recycles. Results appear in Table 3.

In sum, hydroformylation of allyl alcohol in the presence of a conventional Group VIII metal carbonyl complex, a trisubstituted phosphine, a neutral Group VIII(a) metal complex cocatalyst, and optionally, a diphosphinoalkane, gives enhanced reaction rates, satisfactory catalyst lifetimes, and unusually high selectivity to linear aldehydes compared with the same process run in the absence of the neutral Group VIII(a) metal complex cocatalyst.

The preceding examples are meant only as illustrations; the true metes and bounds of the invention are defined by the following claims.

TABLE 1

EFFECT OF CAALYST AND COCATALYST AMOUNTS ON REACTION RATE AND L/B ALDEHYDE RATIO - ALLYL ALCOHOL HYDROFORMYLATION

| | EXAMPLE NO. | | | | | | | | | |
|---|---|---|---|---|---|---|---|---|---|---|
| | C1 | 2 | 3 | 4 | 5 | 6 | 7[4] | 8[5] | C9 | 10 |
| [Rh], ppm | 120 | 120 | 120 | 120 | 120 | 120 | 100 | 80 | 120 | 120 |
| [Fe], ppm | 0 | 305 | 610 | 915 | 1220 | 1525 | 915 | 915 | 0 | 610 |
| DPB[2] used? | Yes | Yes | Yes | Yes | Yes | Yes | Yes | Yes | No | No |
| Relative rate | 1.0 | 1.1 | 1.4 | 1.7 | 1.7 | 1.7 | — | — | 1.3 | 1.6 |
| L/B Aldehyde[3] | 7.5 | 8.0 | 15 | 22 | 32 | 25 | 42 | 37 | 12 | 22 |

[1]Standard conditions: 24 mL allyl alcohol; 200 mL toluene; 1.0 mM $HRh(CO)(PPh_3)_3$; 130 mM triphenylphosphine; 1.0 mM DPB; $H_2/CO$ = 3:1; Reation time: 240 min; temperature: 60° C.
[2]DPB - 1,4-bis(diphenylphosphino)butane
[3]Ratio of linear:branched aldehydes found by gas chromatography
[4]0.83 mM $HRh(CO)(PPh_3)_3$; 108 mM triphenylphosphine; 0.83 mM DPB
[5]0.67 mM $HRh(CO)(PPh_3)_3$; 86.7 mM triphenylphosphine; 0.67 mM DPB
C - indicates comparative example

TABLE 2

EFFECT OF CTALYST RECYCLE ON L/B ALDEHYDE RATIO - ALLYL ALCOHOL HYDROFORMYLATION[1] ($Fe_2(CO)_9$ Cocatalyst)

| | EXAMPLE NO. | | | | | | |
|---|---|---|---|---|---|---|---|
| | 11 | 11A[4] | 11B | 11C | 11D | 11E | 11F |
| [Rh], ppm | | | | 120 | | | |
| [Fe], ppm | | | | 610 | | | |
| DPB[2] used? | | | | Yes | | | |
| L/B Aldehyde[3] | 10 | 13 | 17 | 19 | 14 | 16 | 17 |

[1]Standard conditions: 24 mL allyl alcohol; 200 mL toluene; 1.0 mM $HRh(CO)(PPh_3)_3$; 130 mM triphenylphosphine; 1.0 mM DPB; $H_2/CO$ = 3:1; Reaction time: 240 min; temperature: 60° C.
[2]DPB - 1,4-bis(diphenylphosphino)butane
[3]Ratio of linear:branched aldehydes found by gas chromotography
[4]Runs 11A-11F are consecutive runs with recycled catalyst

TABLE 3

EFFECT OF CATALYST RECYCLE ON L/B ALDEHYDE RATIO - ALLYL ALCOHOL HYDROFORMYLATION[1] (Ru₃(CO)₁₂ Cocatalyst)

| | EXAMPLE NO. | | | | | | | | | | |
|---|---|---|---|---|---|---|---|---|---|---|---|
| | C1 | 12 | 12A[4] | 12B | 12C | 12D | 12E | 12F | 13 | 13A[4] | 13B |
| [Rh], ppm | 120 | | | | 120 | | | | 120 | | |
| [Ru], ppm | 0 | | | | 500 | | | | 500 | | |
| DPB[2] used? | Yes | | | | Yes | | | | No | | |
| Relative rate | 1.0 | 1.5 | | | | | | | 1.0 | | |
| L/B Aldehyde[3] | 7.5 | 11 | 10 | 10 | 13 | 13 | 11 | 13 | 17 | 16 | 15 |

[1]Standard conditions: 24 mL allyl alcohol; 200 mL toluene; 1.0 mM HRh(CO)(PPh₃)₃; 130 mM triphenylphosphine; 1.0 mM DPB; H₂/CO = 3:1; Reaction time: 240 min; temperature: 60° C.
[2]DPB - 1,4-bis(diphenylphosphino)butane
[3]Ratio of linear:branched aldehydes found by gas chromotography
[4]Runs 12A-12F and 13A-13B are consecutive runs with recycled catalyst

We claim:

1. A hydroformylation process which comprises reacting allyl alcohol with hydrogen and carbon monoxide in the presence of a homogeneous catalyst system, wherein the catalyst system comprises a Group VIII metal carbonyl complex catalyst, a trisubstituted phosphine, and a neutral Group VIII(a) metal complex cocatalyst, to produce an aldehyde product mixture having a molar ratio of 4-hydroxybutanal to 3-hydroxy-2-methylpropanal greater than about 10:1.

2. The process of claim 1 wherein the Group VIII metal carbonyl complex catalyst is a rhodium carbonyl complex catalyst.

3. The process of claim 1 wherein the neutral Group VIII(a) metal complex cocatalyst is selected from the group consisting of Fe₂(CO)₉ and Ru₃(CO)₁₂.

4. The process of claim 1 wherein the catalyst system comprises a diphosphinoalkane.

5. The process of claim 4 wherein the diphosphinoalkane is 1,4-bis(diphenylphosphino)butane.

6. The process of claim 1 wherein the process is performed at a temperature within the range of about 25° C. to about 150° C.

7. The process of claim 1 wherein the trisubstituted phosphine is selected from the group consisting of triaryl phosphines, triaryl phosphites, and aryldialkylphosphines.

8. A hydroformylation process which comprises reacting allyl alcohol with hydrogen and carbon monoxide in the presence of a homogeneous catalyst system, wherein the catalyst system comprises a rhodium carbonyl complex catalyst, a trisubstituted phosphine, and a neutral Group VIII(a) metal complex cocatalyst, to produce an aldehyde product mixture having a molar ratio of 4-hydroxybutanal to 3-hydroxy-2-methylpropanal greater than about 10:1.

9. The process of claim 8 wherein the neutral Group VIII(a) metal complex cocatalyst is selected from the group consisting of Fe₂(CO)₉ and Ru₃(CO)₁₂.

10. The process of claim 8 wherein the catalyst system further comprises a diphosphinoalkane.

11. The process of claim 10 wherein the diphosphinoalkane is 1,4-bis(diphenylphosphino)butane.

12. The process of claim 8 wherein the process is performed at a temperature within the range of about 25° C. to about 150° C.

13. The process of claim 8 wherein the trisubstituted phosphine is selected from the group consisting of triaryl phosphines, triaryl phosphites, and aryldialkylphosphines.

* * * * *